US00PP22993P3

(12) United States Plant Patent
Lommerse

(10) Patent No.: US PP22,993 P3
(45) Date of Patent: Aug. 28, 2012

(54) *DAHLIA* PLANT NAMED 'LOMDAHYEL'

(50) Latin Name: ***Dahlia* hybrid**
Varietal Denomination: LOMDAHYEL

(75) Inventor: Henry Lommerse, Mariahout (NL)

(73) Assignee: Lommerse Breeding BV, Mariahout (NL)

( * ) Notice: Subject to any disclaimer, the term of this patent is extended or adjusted under 35 U.S.C. 154(b) by 0 days.

(21) Appl. No.: 12/928,138

(22) Filed: Dec. 2, 2010

(65) Prior Publication Data

US 2012/0144539 P1 Jun. 7, 2012

(51) Int. Cl.
*A01H 5/00* (2006.01)

(52) U.S. Cl. ..... Plt./321

(58) Field of Classification Search ..... Plt./321
See application file for complete search history.

*Primary Examiner* — Annette Para
(74) *Attorney, Agent, or Firm* — Cassandra Bright

(57) ABSTRACT

A new and distinct *Dahlia* cultivar named 'LOMDAHYEL' is disclosed, characterized by distinctive bright yellow flowers, strong, well branched plants producing many flowers. The new variety is a *Dahlia*, normally produced as an outdoor ornamental plant for containers or gardens.

1 Drawing Sheet

Latin name of the genus and species: *Dahlia* hybrid.
Variety denomination: 'LOMDAHYEL'.

BACKGROUND OF THE INVENTION

The new cultivar was discovered as a result of a planned breeding program directed by the inventor, Henry Lommerse a citizen of the Netherlands. The parent is an undistributed, unpatented proprietary variety *Dahlia* hybrid '983898' and the pollen parent is the undistributed, unpatented proprietary variety *Dahlia* hybrid '381205.' The new variety was discovered as a seedling in July 1999, by the inventor in a commercial research greenhouse in Mariahout, the Netherlands.

Asexual reproduction of the new cultivar 'LOMDAHYEL' by vegetative cuttings was first performed in 2008, at a research greenhouse in Mariahout, the Netherlands. Multiple generations have since been produced and have shown that the unique features of this cultivar are stable and reproduced true to type in successive generations.

SUMMARY OF THE INVENTION

The cultivar 'LOMDAHYEL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOMDAHYEL' These characteristics in combination distinguish 'LOMDAHYEL' as a new and distinct *Dahlia* cultivar:

1. Bright yellow inflorescences.
2. Well branched plants.
3. Floriferous habit.
4. Strong, mounding plant habit.

PARENT COMPARISON

Plants of the new cultivar 'LOMDAHYEL' are similar to plants of the seed parent, *Dahlia* hybrid '983898' in most horticultural characteristics, however, plants of the new cultivar 'LOMDAHYEL' produce more flowers, begin flowering earlier in Spring and produce brighter yellow ray florets than '983898'.

Plants of the new cultivar 'LOMDAHYEL' are similar to plants of the pollen parent, *Dahlia* hybrid '381205' in most horticultural characteristics, however, plants of the new cultivar 'LOMDAHYEL' produce larger flowers and have a more compact and mounding plant shape.

COMMERCIAL COMPARISON

'LOMDAHYEL' can be compared to the commercial variety *Dahlia hybrida* 'Dalina Maxi Novia' unpatented. The two varieties are similar in many horticultural characteristics, including having a similar flower color. However, plants of 'LOMDAHYEL' differ in producing flowers with more ray florets, of a brighter yellow. Additionally plants of 'LOMDAHYEL' begin flowering earlier from a rooted cutting than 'Dalina Maxi Novia'. Plant form is also different between the two varieties, with 'LOMDAHYEL' producing more basal branches, and a more round plant shape.

The new variety can also be compared to the commercial variety *Dahlia variabilis*, 'Margaret Improved', U.S. Plant Pat. No. 14,202. *Dahlia* 'LOMDAHYEL' and *Dahlia* 'Margaret Improved' are similar in many horticultural characteristics, including a similar flower color. However, plants of 'LOMDAHYEL' are more vigorous, produce more flowers and branches per plant, and larger flowers than 'Margaret Improved'.

BRIEF DESCRIPTION OF THE PHOTOGRAPH

The accompanying photograph in FIG. 1 illustrates in full color a typical plant of 'LOMDAHYEL' grown in a outdoors, in Mariahout, the Netherlands, in a commercial 20 cm container.

Age of the plant photographed is approximately 70 days from a rooted cutting.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'LOMDAHYEL' plants grown outdoors, in the ground during the Summer months in Mariahout, the Netherlands. The growing temperature ranged from 16° C. to 27° C. daytime and 16° to 18° C. at night. One treatment of the growth regulator daminozide 85% at a rate of approximately 0.1%, was applied at approximately 2 weeks after planting the rooted cutting. Measurements and numerical values represent averages of typical plant types.

Botanical classification: *Dahlia* hybrid 'LOMDAHYEL.'

PROPAGATION

Time to initiate roots:
- *Summer.*—13-15 days days at approximately 20-18 (day-night) ° C.
- *Winter.*—19-23 days at approximately 18-16 (day-night) ° C.

Root description: Fibrous.

Tuber description:
- *Average length.*—10.9 cm, average thickness: 1.1 cm, Colored near RHS Greyed-Yellow 161D.

Propagation method: Vegetative cuttings.

PLANT

Age of plant described: 70 days from a rooted cutting.

Growth habit: Broad inverted triangular, broad upright.

Pot size of plant described: Field grown.

Height: Approximately 44.5 cm.

Plant spread: Approximately 52.5 cm.

Growth rate: Moderate.

Branching characteristics:
- *Length of primary lateral branches.*—Approximately 29.3 cm.
- *Quantity of lateral branches.*—Approximately 33.
- *Characteristics of primary lateral branches.*—Diameter: Approximately 0.4 cm. Color: Near RHS Yellow-Green 144A. Texture: Smooth, moderately glossy. Strength: Moderately strong.
- *Internode length.*—Average 5.4 cm.

FOLIAGE

Leaf:
- *Arrangement.*—Single to cleft in three lobes, opposite.
- *Shape.*—Overall shape ovate.
- *Quantity.*—Approximately 10 pairs per branch.
- *Average overall length.*—Approximately 7.3 cm.
- *Average overall width.*—Approximately 6.5 cm.

Individual leaf blades:
- *Shape of blade.*—Ovate.
- *Apex.*—Apiculate.
- *Base.*—Acuminate.
- *Margin.*—Coarsely serrate.
- *Appearance of surfaces.*—Matte.
- *Pubescence.*—No leaf pubescence on upper side; under side and margins sparsely pubescent, average length of hairs: 0.2 mm, colored green-white, too small to be measured with R.H.S.-Colour Chart.
- *Leaf attachment angle.*—Leaves placed in an average angle of 25° to lateral branch.
- *Color.*—Young foliage upper side: Near RHS Green N137C. Young foliage under side: Near RHS Yellow-Green 147B. Mature foliage upper side: Near RHS Green137A. Mature foliage under side: Near RHS Yellow-Green 148B.
- *Venation.*—Type: Pinnate. Venation color upper side: Near RHS Yellow-Green 147B. Venation color under side: Near RHS Yellow-Green 147B.
- *Petiole.*—Length: 3.6 cm. Diameter: 0.2 cm. Color: Near RHS Yellow-Green 144B. Texture: Smooth, glossy. No stipules present.

FLOWER

Natural flowering season: Spring through Summer.

Days to flowering from rooted cutting: Ten weeks.

Inflorescence and flower type and habit: Fully double, straight on top of peduncle (average angle 0°) to outward (average angle 70°).

Rate of flower opening: 14 to 21 days from bud to fully opened flower.

Flower longevity on plant: Approximately 2 weeks.

Persistent or self-cleaning: Persistent.

Bud:
- *Shape.*—Flattened globular.
- *Length.*—0.7 cm.
- *Diameter.*—0.9 cm.
- *Color.*—Near RHS Green143B, base darker; 143A.

Flower size:
- *Diameter.*—Approximately 11.2 cm.
- *Depth.*—Approximately 3.5 cm.

Ray florets:
- *Quantity.*—Approx. 120.
- *Arrangement.*—Rotate, in 6 rows.
- *Length.*—4.7 cm.
- *Width.*—2.1 cm.
- *Shape.*—Obovate, base fused.
- *Apex.*—Obtuse.
- *Base.*—Cuneate.
- *Margin.*—Entire.
- *Texture and appearance, upper and lower surfaces.*—Smooth, slightly velvety, dull.
- *Color.*—When opening, upper surface: Near RHS Green-Yellow 1A. When opening, lower surface: Near RHS Green-Yellow 1B. Fully opened, upper surface: Near RHS Yellow 2A. Fully opened, lower surface: Near RHS Yellow 2B.

Disc florets:
- *Quantity.*—Approx. 7, in center of flwoer.
- *Length.*—Approximately 0.8 cm.

*Width*.—0.1 cm.
*Shape*.—Cylindric.
*Apex*.—Obtuse.
*Base*.—Fused.
*Margin*.—Entire.
*Texture and appearance, upper and lower surfaces*.—Shiny.
*Color*.—When opening, all surfaces: Near RHS Green-Yellow 1B. Fully opened, all surfaces: Near RHS Green-Yellow 1B.

Phyllaries/involucral bracts:
*Quantity*.—8.
*Length*.—Approximately 1.4 cm.
*Width*.—Approximately 0.6 cm.
*Shape* (*overall*).—Ovate to elliptic.
*Apex*.—Subacute.
*Base*.—Cuneate.
*Margin*.—Entire.
*Color*.—Near RHS Green 137B.

Peduncles:
*Length*.—Average 10.3 cm.
*Diameter*.—Approximately 0.3 cm.
*Angle*.—About 0° to the lateral branch, straight on top of lateral branch).
*Strength*.—Strong.
*Texture*.—Non pubescent.
*Color*.—Near RHS Yellow-Green 144A.
*Strength*.—Strong.

Fragrance: Faint.

REPRODUCTIVE ORGANS

Stamens:
*Number*.—Average of 7 disc florets in the centre of the inflorescence with an average of 4 deformed stamen per disc floret.

Anthers:
*Shape*.—Linear.
*Length*.—Approximately 0.4 cm.
*Color*.—Near RHS Yellow 14A.
*Pollen*.—None observed.

Pistil: No pistil present.

OTHER CHARACTERISTICS

Seeds and fruits: Not observed to date.

Disease/pest resistance: Neither resistance nor susceptibility to pathogens and pests common to *Dahlia* have been observed.

Temperature tolerance: The new variety tolerates temperatures between 10 to 35° C.

What is claimed is:

1. A new and distinct cultivar of *Dahlia* plant named 'LOMDAHYEL' as herein illustrated and described.

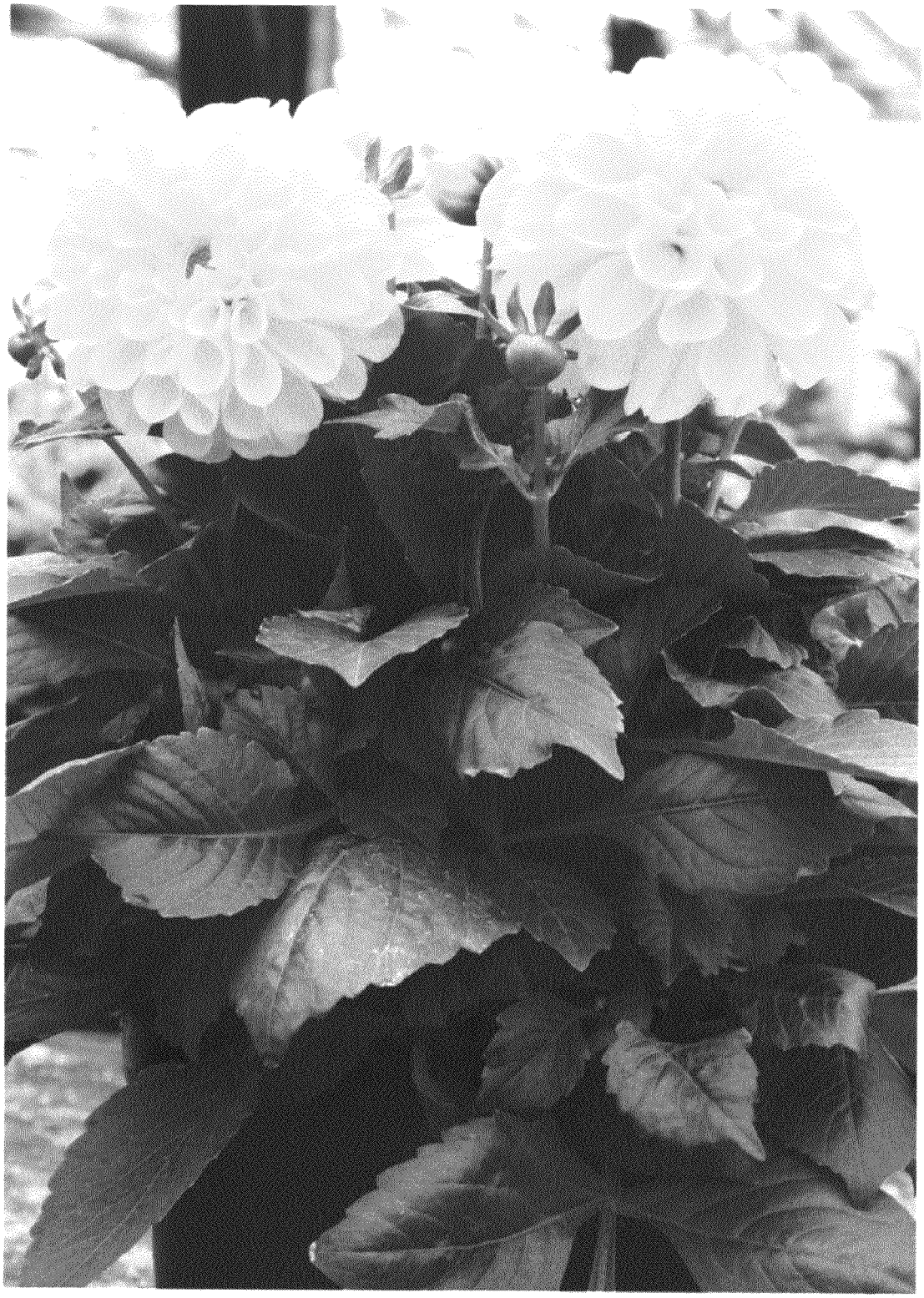

* * * * *